(12) United States Patent
Sumiya

(10) Patent No.: US 6,585,723 B1
(45) Date of Patent: *Jul. 1, 2003

(54) CORNEAL SURGERY APPARATUS

(75) Inventor: Toshifumi Sumiya, Aichi (JP)

(73) Assignee: Nidek Co., Ltd., Aichi (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/388,924

(22) Filed: Sep. 2, 1999

(30) Foreign Application Priority Data

Sep. 4, 1998 (JP) .......................... 10-251520
Jun. 3, 1999 (JP) .......................... 11-156102

(51) Int. Cl.[7] ................................. A61F 9/07
(52) U.S. Cl. ..................... 606/5; 606/10; 606/12; 606/13
(58) Field of Search ................. 606/3–13; 351/206–212

(56) References Cited

U.S. PATENT DOCUMENTS

| | | |
|---|---|---|
| 4,209,252 A | 6/1980 | Arditty et al. |
| 4,665,913 A | 5/1987 | L'Esperance, Jr. |
| 4,721,379 A | 1/1988 | L'Esperance |
| 4,838,682 A | 6/1989 | Portnoy |
| 5,098,426 A * | 3/1992 | Sklar et al. ............... 606/10 |
| 5,491,524 A * | 2/1996 | Hellmuth et al. ........... 351/212 |
| 5,500,697 A | 3/1996 | Fujieda |
| 5,507,799 A | 4/1996 | Sumiya |
| 5,562,656 A | 10/1996 | Sumiya |
| 5,637,109 A | 6/1997 | Sumiya |
| 5,906,608 A | 5/1999 | Sumiya et al. |

FOREIGN PATENT DOCUMENTS

| | | |
|---|---|---|
| EP | 0 765 648 | 4/1997 |
| JP | 9-149914 | 6/1997 |

* cited by examiner

*Primary Examiner*—David M. Shay
(74) *Attorney, Agent, or Firm*—Finnegan, Henderson, Farabow, Garrett & Dunner, L.L.P.

(57) ABSTRACT

In a corneal surgery apparatus, a corneal shape measurement unit for measuring a three-dimensional shape of a cornea includes a measurement light projecting optical system for projecting measurement light onto the cornea and its convergent point is shifted by moving a focusing lens along an optical axis, a measurement light receiving optical system including a photo-detector for receiving reflected light from the cornea and its convergent point is shifted by moving a focusing lens along an optical axis, a scanning unit for shifting a projection spot of the measurement light on the cornea in XY directions and an arithmetic unit for performing arithmetic to obtain the three-dimensional shape of the cornea from a position of the projection spot, a result detected by the photo-detector and a position to which the focusing lens is moved.

11 Claims, 6 Drawing Sheets

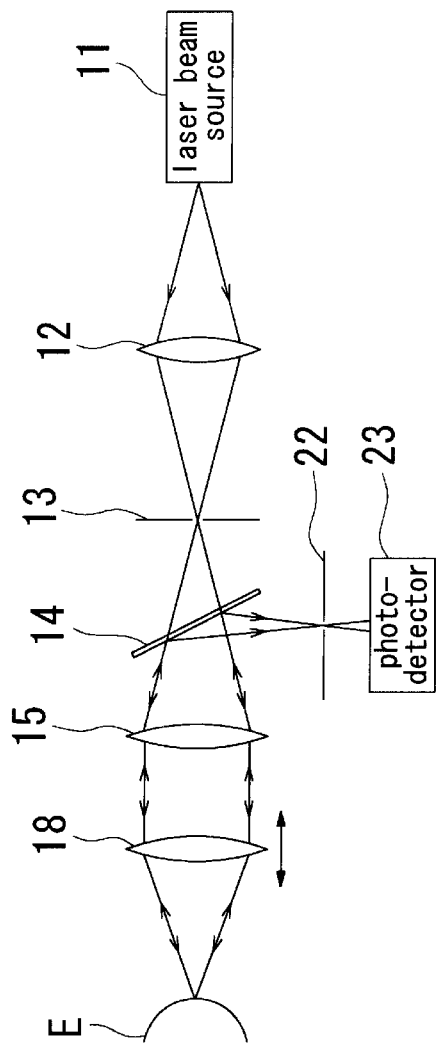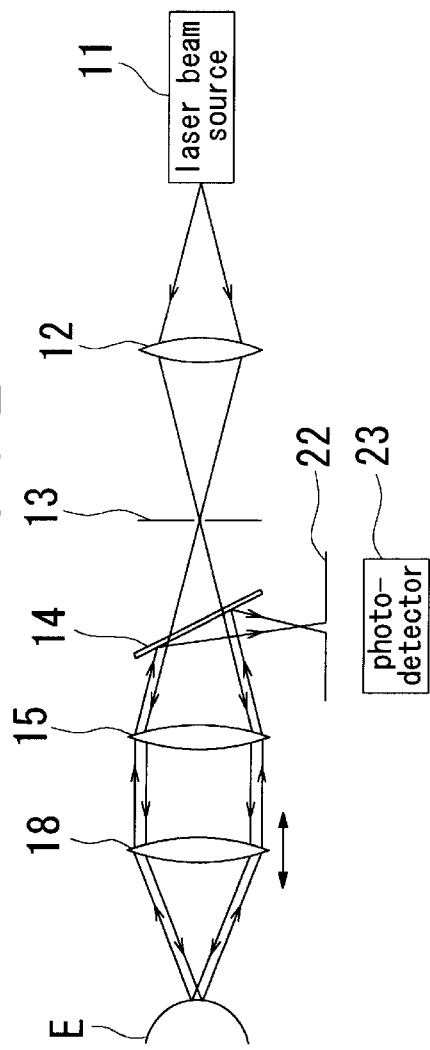

CORNEAL SURGERY APPARATUS

BACKGROUND OF THE INVENTION

1. Field of the Invention

The present invention relates to a corneal surgery apparatus for ablating a part of a cornea of a patient's eye to correct a refractive error of the eye or to remove a lesion therefrom.

2. Description of Related Art

Conventionally known is a corneal surgery apparatus that ablates a corneal stroma of a patient's eye with an excimer laser or the like to change a refractive power of the eye to correct ametropia including myopia, hypermetropia, astigmatism and the like, or to remove an affected part of the cornea such as opacity. Also known is a corneal shape measurement apparatus (hereinafter referred to as a topography apparatus) that projects a placido ring onto a cornea and photographs an image of the placido ring to measure the corneal surface shape. Further, it has also been suggested to input the corneal shape data obtained by the topography apparatus to a corneal surgery apparatus. An amount to be ablated is calculated from the data and also the post-operative refractive power to be obtained. The ablation is carried out in accordance with the calculated ablation amount.

However, the above-described way presents the following problems. One of the problems lies in the case of measuring a corneal shape of a patient's eye by a topography apparatus first, and then performing surgery to correct the refractive power by a separate corneal surgery apparatus based on the data captured from the topography apparatus. In this case, the positional relationship between the topography apparatus and the patient's eye is not necessarily the same as the positional relationship between the corneal surgery apparatus and the patient's eye. It is especially so, when the measurement by the topography apparatus is carried out with the patient being sit and fixed by the face, while the surgery by the corneal surgery apparatus is carried out with the patient being laid on his back. Due to the inclination of the face, the gravity and other various factors, it is often the case that the patient's eye is not in a uniform state. This results in the possibility of ablating an unintended part of the cornea. In this case, the post-operative corneal shape may differ from the expected one and the refractive error may not be corrected as expected.

One possible way to address the above problem is to combine the corneal surgery apparatus and the topography apparatus into one apparatus so as to make the topography position and the corneal surgery position coincide with each other relative to the patient's eye. However, an attempt to make one apparatus by combining the topography apparatus including a placido ring projecting unit and a TV camera for photographing its corneal reflex and the like with the corneal surgery apparatus including a laser irradiation optical system and an observation optical system will results in an undesirably large apparatus.

SUMMARY OF THE INVENTION

The present invention has been made in view of the above circumstances and has an object to overcome the above problems and to provide an apparatus for corneal surgery which is small and compact, while being capable of preventing displacement between a corneal shape measurement position and a laser beam irradiation position upon corneal surgery to remove a part of the cornea with a laser.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, a corneal surgery apparatus which ablates corneal tissue with a laser beam, the apparatus comprises an irradiation unit including a light directing optical system for directing the laser beam to an intended range on a cornea of a patients s eye, wherein the laser beam has a wavelength in a far ultra—violet region and intensity capable of causing ablation and a corneal shape measurement unit, provided inside the apparatus, for measuring a three-dimensional shape of the cornea, the corneal shape measurement unit including a measurement light projecting optical system for projecting measurement light onto the cornea and its convergent point is shifted by moving a focusing lens along an optical axis, a measurement light receiving optical system including a photo-detector for receiving reflected light from the cornea and its convergent point is shifted by moving a focusing lens along an optical axis, a scanning unit for shifting a projection spot of the measurement light on the cornea in XY directions and an arithmetic unit for performing arithmetic to obtain the three-dimensional shape of the cornea from a position of the projection spot, a result detected by the photo-detector and a position to which the focusing lens is moved.

As described above according to the present invention, it is possible to prevent the displacement between the corneal shape measurement position and the laser irradiation spot upon corneal laser surgery to remove a portion of the cornea. Simultaneously, it is also possible to make the whole apparatus compact in size. In addition, according to the present invention, the corneal thickness can be measured so that judgement on ablation or adjustment of the ablation amount may be made based on the measured corneal thickness.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIGS. 6A and 6B are views explaining difference in light quantity due to the deviation of the measurement light on the cornea in the direction of the thickness.

DETAILED DESCRIPTION OF THE PREFERRED EMBODIMENTS

A detailed description of one preferred embodiment of a corneal surgery apparatus embodying the present invention will now be given referring to the accompanying drawings.

Overall Configuration

Figure 1:
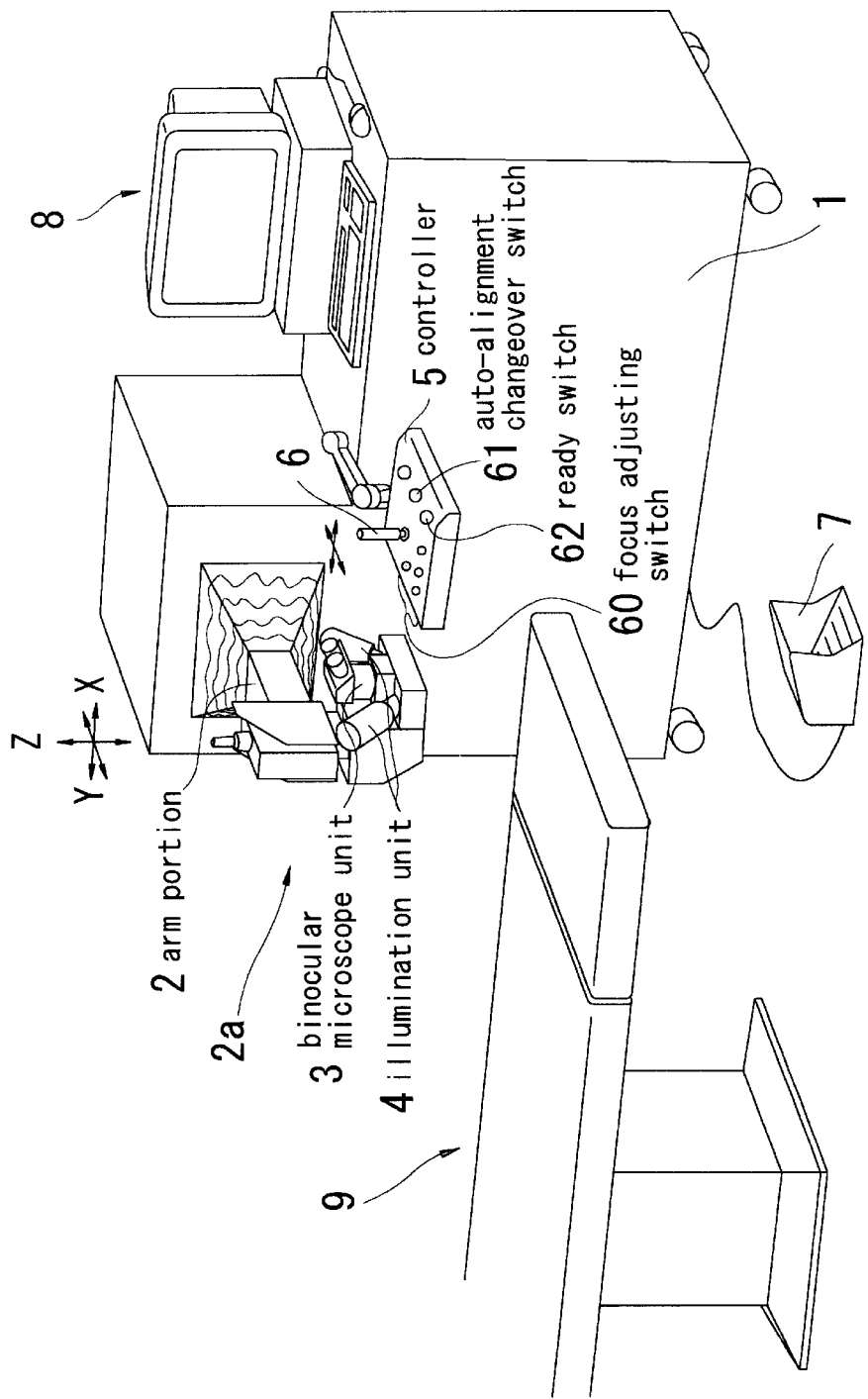
FIG. 1 is a view showing an overall configuration of a corneal surgery apparatus of the present invention.

FIG. 1 is a view showing an overall configuration of a corneal surgery apparatus of the present invention. The reference numeral 1 is a main body of the surgery apparatus and optical systems and a control system are partially embedded therein. 2 is an arm portion for directing a laser beam to a patient's eye. An end portion 2a of the arm portion 2 is provided with a binocular microscope unit 3 for observing the patient's eye, an illumination unit 4 and the like. The end portion 2a may be moved in X, Y and Z directions by a driving device. For the details of this arm portion 2 (the end portion 2a) and its driving devise, see Japanese Published unexamined Patent Application HEI 9-149914 that corresponds to U.S. patent application Ser. No. 08/979,846 and also to EP Published Unexamined Patent Application 0765648 by the present applicant.

5 is a controller provided with a joystick 6 for signaling to move the arm portion 2 (the end portion 2a) in X and Y directions and also with various operation switches. 7 is a foot switch for signaling to irradiate a laser beam. 8 is a computer to perform input of various data about surgical conditions as well as to perform arithmetic, storage and display of corneal shape data, ablation data and the like. 9 is a bed on which the patient lies down.

Configuration of Each System

Figure 2:
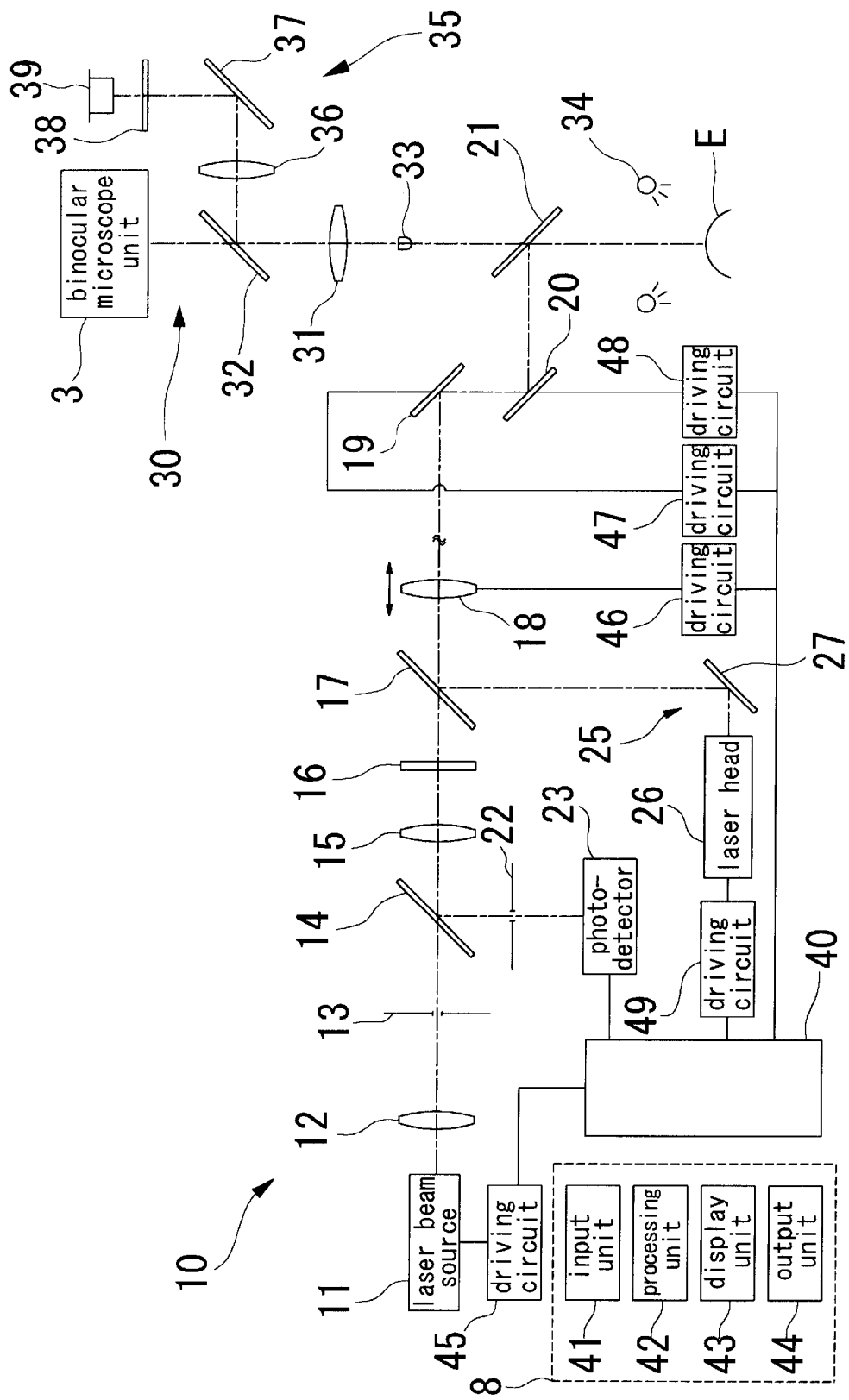
FIG. 2 is a view showing a schematic configuration of an optical system and a control system provided in the corneal surgery apparatus of the present invention.

FIG. 2 is a view showing a schematic configuration of the optical systems and the control system of the corneal surgery apparatus of the present invention. Concerning the optical systems, descriptions are given separately to a corneal shape measurement optical system, a laser irradiation optical system, an observation optical system and an eyeball position detecting optical system.

(A) Corneal Shape Measurement Optical System 10 is the corneal shape measurement optical system for measuring a three-dimensional corneal shape. 11 is a laser beam source for emitting a laser beam which functions as measurement light to measure the corneal shape. In this embodiment, an infrared semiconductor laser beam source that emits infrared laser at a wavelength of 800 nm is used. The measurement light does not necessarily have to be infrared light, yet it is advantageous in that infrared light is not glaring and therefore the discomfort of the patient upon a measurement is reduced. 12 is a focusing lens, 13 is a pinhole (aperture) and 14 is a polarizing beamsplitter. 15 is a collimating lens that makes the infrared laser beam a parallel beam and 16 is a quarter waveplate.

17 is a dichroic mirror by which an optical axis of a laser irradiation optical system 25 described later is made coaxial with an optical axis of the measurement optical system 10. The dichroic mirror 17 transmits the infrared laser beam that the laser beam source 11 emits but reflects an excimer laser beam that an excimer laser head 26, mentioned later, emits. 18 is a focusing lens for focusing the infrared laser beam and the excimer laser beam. The lens 18 is arranged movably back and forth along the optical axis. 19 and 20 are scanning mirrors which scan the infrared laser beam and the excimer laser beam over the cornea in two-dimensional directions. In this embodiment, a galvano-mirror is used as the scanning mirrors 19 and 20 respectively.

21 is a dichroic mirror by which the common optical axis of the measurement optical system 10 and the laser irradiating optical system 25 is made coaxial with a common optical axis of an observation optical system 30 and an eyeball position detecting optical system 35 described later. The dichroic mirror 21 reflects the infrared laser beam having a wavelength of 800 nm emitted from the laser beam source 11 as well as the excimer laser beam having a wavelength of 193 nm, but transmits visible light having a wavelength in a range of about 400–700 nm as well as the infrared laser beam having a wavelength of 950 nm emitted from infrared illumination light sources 34 described later. The reference letter E denotes a/the cornea of the patient's eye. The scanning mirrors 19 and 20, and also the dichroic mirror 21 are provided inside the end portion 2a.

22 is a pinhole (aperture), 23 is a photo-detector that detects the infrared laser beam being measurement light reflected from the cornea E. The pinhole 13 and the pinhole 22 are arranged to be conjugate with each other relative to the cornea E. It should be noted that the lens 18 also serves the function of making the reflected light from the cornea E parallel light and the lens 15 also serves the function of focusing/converging the reflected light.

(B) Laser Irradiating Optical System 25 is the laser irradiation optical system for irradiating a laser beam to ablate a cornea. A laser head 26 irradiates a laser beam, which has no thermal effect on a corneal tissue, for ablation upon corneal surgery. Used in this embodiment is an ArF excimer laser head that emits an ArF excimer laser beam having a wavelength of 193 nm. This therapeutic laser beam has to be a laser beam having its wavelength in a far ultraviolet region to ablate corneal tissue. It is desirable to use a laser beam having a wavelength of 150–230 nm, and more preferably, an ArF laser beam having a wavelength of 193 nm. 27 is a mirror that reflects the excimer laser beam emitted from the laser head 26. The excimer laser beam emitted from the laser head 26 is reflected and deflected first by the mirror 27 and then by the dichroic mirror 17. Thereafter, the excimer laser beam passes through the lens 18 and is sequentially reflected and deflected by the scanning mirrors 19 and 20, and finally by the dichroic mirror 21, thereby being directed onto the cornea E.

(C) Observation Optical System 30 is the observation optical system for observing the patient's eye. 31 is an objective lens. 32 is a dichroic mirror that transmits visible light, but reflects the infrared light having a wavelength of 950 nm emitted by the infrared illumination light sources 34. Visible illumination light from the illumination unit 4 illuminates an anterior part of the patient's eye and forms an image thereof. Luminous flux of the image passes through the dichroic mirror 21, the lens 31 and the dichroic mirror 32, and then enters the microscope unit 3. Consequently, a surgeon can observe the patient's eye with the binocular microscope unit 3. In addition, the observation optical system 30 includes a not illustrated reticle plate inserted therein. This allows to provide a reference for alignment of the patient's eye in X and Y directions.

Also included in the observation optical system 30 is a target projecting optical system comprising two slits (reference may be made to Japanese Published unexamined Patent Application HEI 6-47001 that corresponds to U.S. Pat. No. 5,562,656 by the present applicant). The observation optical system 30 is arranged inside the end portion 2a. 33 is a fixation light arranged on the optical axis of the observation optical system 30 and emits visible light.

(D) Eyeball Position Detecting Optical System 35 is the eyeball position detecting optical system for detecting the eyeball position of the patient's eye. 34 are the infrared illumination light sources which emit infrared light at a wavelength of 950 nm and a total of four illumination light sources 34 are arranged at 90 intervals about the optical axis. 36 is a photographing lens and 37 is a mirror. 38 is an infrared light transmitting filter to cut off noise light. 39 is a CCD camera. The eyeball position detecting optical system 35 is also arranged inside the end portion 2a.

The luminous flux of the image of the anterior part of the patient's eye illuminated by the illumination light sources 34 passes through the dichroic mirror 21 and the lens 31, and then is reflected by the dichroic mirror 32. Thereafter, the luminous flux passes through the photographing lens 36 thereby forming an image on a photographing surface of the camera 39 via the mirror 37 and the filter 38. Upon the passage of the luminous flux, the filter 38 cuts off the visual light reflected slightly by the dichroic mirror 32.

Figure 3:
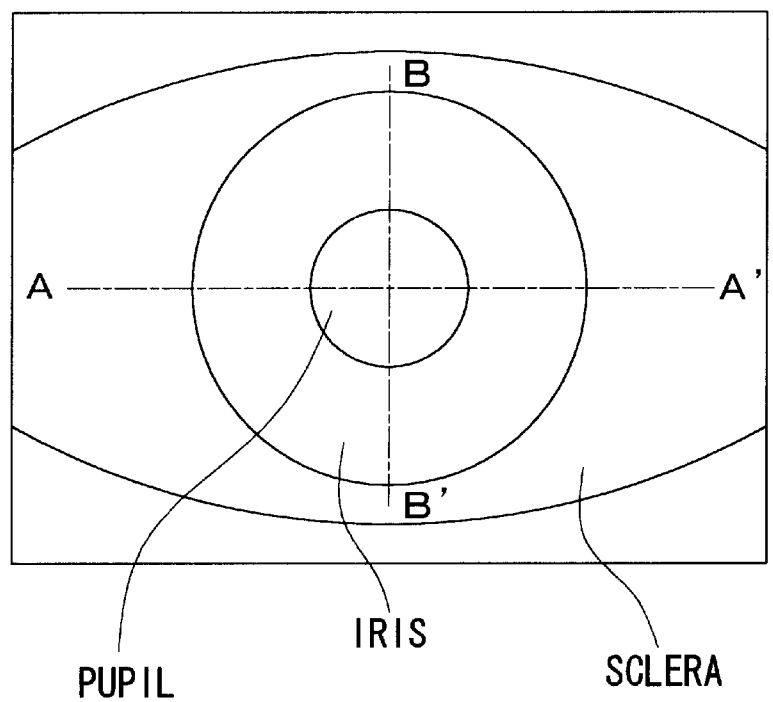
FIG. 3 is a view showing an image of an anterior part of the patient's eye that a CCD camera receives.
Figure 4:
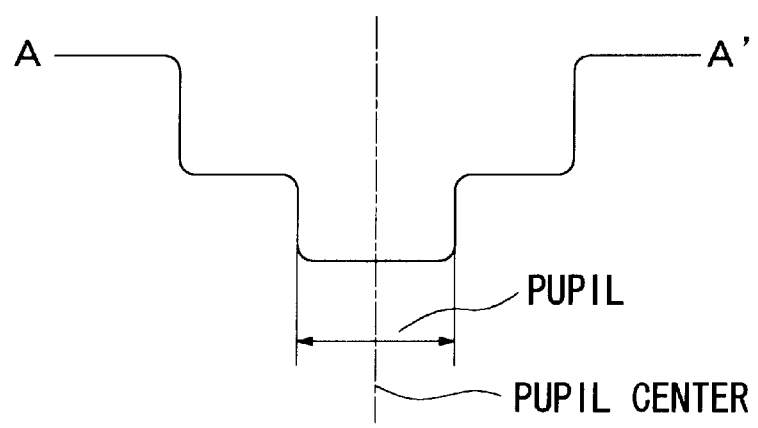
FIG. 4 is a view showing light distribution along a line A–A'.

The camera 39 detects the eyeball position in the following way. FIG. 3 is a view showing the image of the anterior part of the eye captured by the camera 39 and FIG. 4 is a view showing distribution of the light along the line A–A' (shown in FIG. 3) obtained from photographing signals of the camera 39. As shown in FIG. 4, the light distribution differs depending on its corresponding part of the eye such as a pupil, an iris and a sclera. Accordingly, from information about the light distribution, coordinates of each pupil edge along its lateral direction are detect. Further, from the coordinates of the pupil edge detected thereby, coordinates of its center in the lateral direction are as well obtained. Similarly, coordinates of a center of the pupil in its vertical direction are obtained from information about the light distribution along the vertical line B–B' (shown in FIG. 3). That is to say, the light distribution along the two lines allows to locate the pupil center with respect to the optical axis of the detecting optical system 35 (equally meaning the optical axes of the measurement optical system 10 and the irradiating optical system 25) being adjusted to have a predetermined positional relationship on the photographing element of the camera 39.

(E) Control System 40 is a control system embedded within the main body 1. The control system 40 drives and controls the laser beam source 11, the lens 18, the scanning mirrors 19 and 20, the laser head 26, the fixation light 33, the illumination light sources 34 and the like. 41, 42, 43, 44 are respectively an input unit (a key board, a mouse and the like), a arithmetic analytical processing unit (CPU and the like), a display unit (a monitor), and an output unit (a printer, a floppy disk drive and the like) all of which are provided to the computer 8. The input unit 41 is used to input laser irradiation conditions such as an intended post-operative refractive power, a corneal radius and the like. The processing unit 42 processes signals from the photo-detector 23 thereby obtaining corneal shape data. The processing unit 42 also processes the corneal shape data and the inputted irradiation conditions thereby obtaining ablation data such as an amount of the cornea to be ablated and the like. The data processed by the processing unit 42 is sent to the control unit 40. Base on the processed data, the control unit 40 drives and controls the scanning mirrors 19 and 20, the laser head 26 and the like. The display unit 43 displays both the pre-operative corneal shape and post-operative corneal shape along with other information in accordance with the corneal shape data sent from the processing unit 42. The output unit 44 outputs various obtained data.

45 is a driving circuit for the laser beam source 11, 46 is a driving circuit for the lens 18, 47 and 48 are driving circuits for the scanning mirrors 19 and 20 respectively, and 49 is a driving circuit for the laser head 26 (driving circuits for the fixation light 33 and the illumination light sources 34 are not illustrated). A driving circuit for the arm portion 2 is also controlled by the control unit 40.

Hereinafter, descriptions are given to operations of the apparatus with the above described configuration The descriptions focus on surgery for correcting a refractive error.

The surgeon first makes the patient lie on the bed 9 and places the arm portion 2 (the end portion 2a) above the patient's eye. Thereafter, the surgeon lights the illumination unit 4, the fixation light 33, the illumination light sources 34 and the like and then makes the patient's eye fixate at the fixation light 33. While observing the anterior part of the patient's eye being illuminated by the illumination unit 4 with the microscope unit 3, the surgeon operates the joystick 6 to make alignment in X and Y directions so as to bring a not illustrated reticle and the pupil into a predetermined positional relationship with each other. In addition, the surgeon operates a focus adjusting switch 60 to perform alignment in a Z direction. When signals generated in response to the operations of the joystick 6 (and the switch 60) are inputted to the control unit 40, the control unit 40 actuates the driving circuit for the arm portion 2 so as to move the arm portion 2 (the end portion 2a) in X and Y directions (and also in a Z direction).

During the alignment, if an auto-alignment changeover switch 61 provided on the controller 5 is turned on, an auto-alignment starts. When the patient's eye is in a range where the pupil center is detectable by the detecting optical system 35, the control unit 40 moves the arm portion 2 (the end portion 2a) in X and Y directions so as to bring the optical axes of the measurement optical system 10 and the irradiating optical system 25 into coincidence with the pupil center.

To perform the corneal shape measurement or irradiation of the laser, while keeping the optical axes of the measurement optical system 10 and the irradiating optical system 25 into coincidence with the pupil center, the surgeon depresses a ready switch 62 provided on the controller 5 after turning on the auto-alignment changeover switch 61 and completing the alignment. When the ready switch 62 is depressed, a predetermined position on the photographing element is stored as a reference position and an eyeball tracking mechanism (auto-tracking) is actuated thereby moving the arm portion 2 (the end portion 2a) so as to bring the reference position into coincidence with the pupil center. For the details of the auto-alignment and the auto-tracking, see Japanese Published Unexamined Patent Application HEI 9-149914 that corresponds to U.S. patent application Ser. No. 08/979,846 and also to EP Published Unexamined Patent Application 0765648 by the present applicant.

When the alignment of the patient's eye is completed, a three-dimensional shape of the cornea E is measured by the measurement optical system 10. The infrared laser beam of the linearly polarized light emitted from the laser beam source 11 converges via the lens 12 on the pinhole 13. After converging and passing through the pinhole 13, the infrared laser beam passes though the beam splitter 14, because the laser beam source is arranged to adapt its polarization direction, and then is made parallel light by the lens 15. Thereafter, the linearly polarized light is converted into circularly polarized light by the quater waveplate 16, which is arranged to form an angle of 45° between its retarder principal plane and the polarization plane of the infrared laser beam. Next, the infrared laser beam passes through the dichroic mirror 17 and converges via the lens 18. Finally, the infrared laser beam is successively reflected and deflected by the scanning mirrors 19 and 20 to converge in the vicinity of the cornea E. Through controlling the reflection angles (deflection angles) of the scanning mirrors 19 and 20, the infrared laser beam comes to scan in two-dimensional directions.

Figure 5:
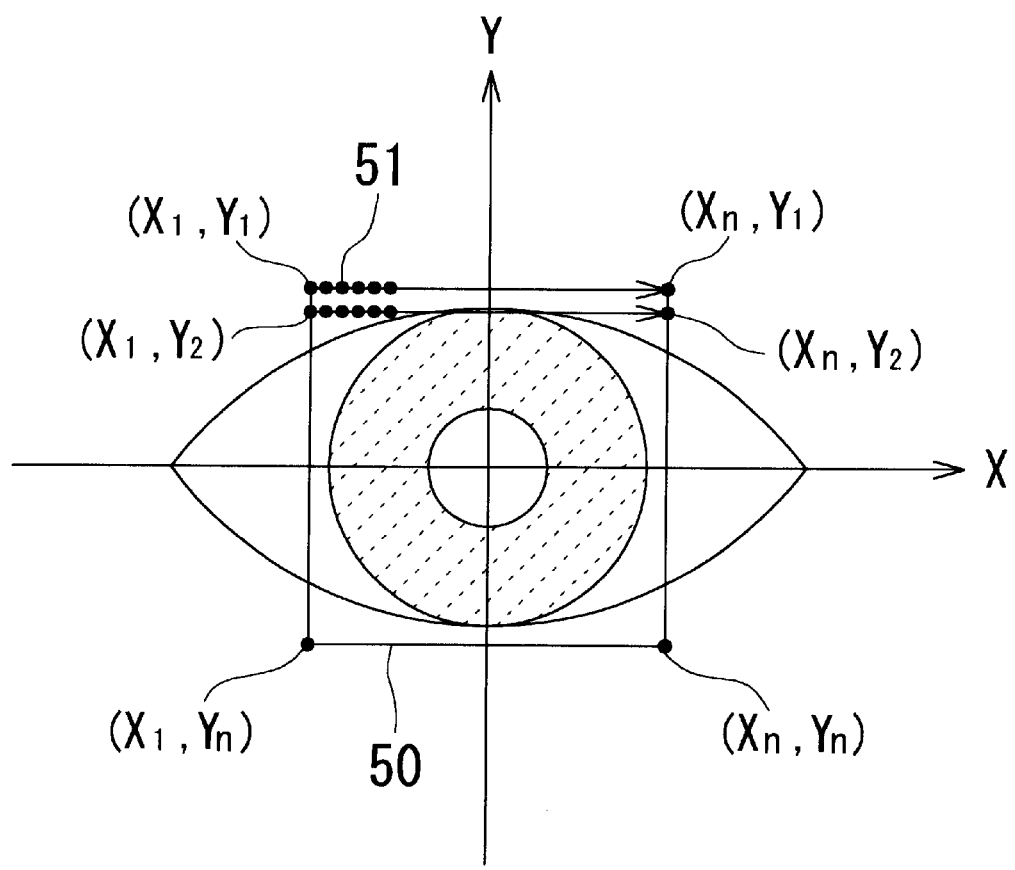
FIG. 5 is a view explaining a scan of the measurement light over the cornea in two-dimensional directions.

Here, descriptions are given to the scan of the infrared laser beam by the scanning mirrors 19 and 20 over the cornea E in two-dimensional directions. FIG. 5 is a view explaining the scan with the measurement light over the cornea in two-dimensional directions. The control unit 40 drives the scanning mirrors 19 and 20 via the respective driving circuits 47 and 48 thereby scanning the infrared laser beam 51 being the measurement light over a scanning range starting from the top left to the bottom right in succession of $(X_1, Y_1) \ldots (X_0, Y_1), (X_1, Y_2) (X_n, Y_2)-(X_1, Y_n) \ldots (X_n, Y_n)$.

While diverging, the infrared laser beam reflected by the cornea E is reflected and deflected successively by the scanning mirrors 20 and 19 and then made to be parallel beam again by the lens 18. Thereafter, the infrared laser beam passes through the dichroic mirror 17 and is converted from circularly polarized light into linearly polarized light by the quater waveplate 16. After being converged by the lens 15, the infrared laser beam of the linearly polarized light is reflected by the polarizing beamsplitter 14 because its polarization direction is rotated 90° from the polarization direction at the time the infrared laser beam runs toward the cornea E. The infrared laser beam converges on, and passes through, the pinhole 22 and enters into the photo-detector 23.

When the corneal surface (anterior surface or posterior surface) is on the two-dimensional flat surface (or may be curved surface) over which the convergent point of the infrared laser beam scans, as shown in FIG. 6A, the infrared laser beam reflected therefrom goes back through the same optical path as described above and converges on the pinhole 22. As the result, relatively large quantity of light enters into the photo-detector 23. On the contrary, when the corneal surface (anterior surface or posterior surface) is not on the two-dimensional flat surface (or may be curved surface) over which the convergent point of the infrared laser beam scans, in other words when the infrared laser beam is reflected off the convergent point, as shown in FIG. 6B, the reflected infrared laser beam does not converge on the pinhole 22 and become blurred. As the result, almost no light enters into the photo-detector 23. Accordingly, when scanning the convergent point of the infrared laser beam over the two-dimensional flat surface, the reflected light is sufficiently detected by the photo-detector 23 only where the corneal surface is within the surface. This allows to obtain a contour of the cornea E on the surface. The pinholes 13 and 22 are arranged to be conjugate with each other relative to the cornea E, and thereby forming a confocal optical system (that is to say a point light source and a point detector are in image forming relation with each other relative to one point of an object).

Further, the control unit 40 moves the lens 18 via the driving circuit 46 along the optical axis so that the two-dimensional flat surface over which the convergent point of the infrared laser beam scans is gradually shifted in the direction of the thickness of the cornea. The contour of the cornea E on the surface is measured repeatedly in the same way mentioned above but gradually shifted in the direction of the thickness. By combining the obtained contours of the cornea E on the surface into a three-dimensional shape, three-dimensional shapes of the anterior and the posterior cornea E are obtained.

Figure 7:
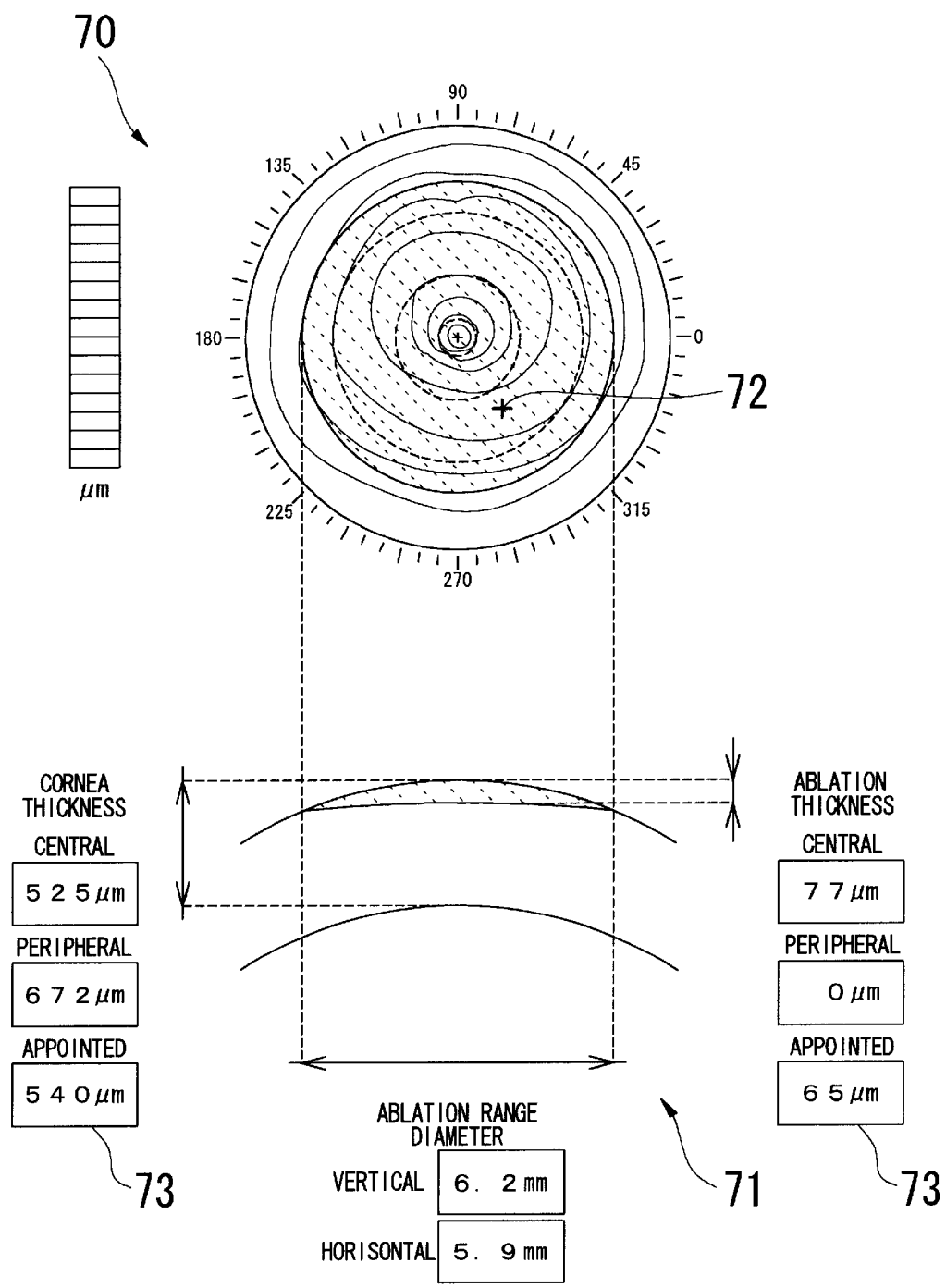
FIG. 7 is an example displaying measured corneal shape data and an obtained ablation amount.

Detection signals from the photo-detector 23 are fed into the processing unit 42 via the control unit 40 and the processing unit 42 obtains three-dimensional corneal shape data based on the detection signals and irradiation spots by the infrared laser beam in three-dimensional directions (the irradiation spots are calculated from the deflection angles of the scanning mirrors and the position of the lense 18). In addition, the corneal thickness is obtained based on the anterior and posterior shapes of the cornea E. In accordance with the corneal shape data and the corneal thickness data obtained thereby, a map 70, a sectional view 71 and other numeral data (see FIG. 7) are displayed on the display unit 43.

After completing the corneal shape measurement by the measurement optical system 10, the surgeon inputs intended post-operative corneal data such as refractive power, corneal radius and the like with the use of the input unit 41 (the data may be inputted in advance). The processing unit 42 determines ablation data such as necessary amount to be ablated and the like to correct refractive error based on the corneal shape data obtained through the measurement by the measurement optical system 10 and the post-operative corneal data inputted by the surgeon. The ablation data determined thereby is displayed on the display unit 43 in superposed relation with the map 70 and the sectional image 71 and other data. Also, the ablation thickness (ablation depth) and the ablation range are displayed numerically. (See FIG. 7.) In addition, the predicted post-operative refractive power and corneal radius are also displayed (not illustrated). Further, it is possible to designate a desired point by moving a cursor 72 on the map 70 so as to display corneal thickness and ablation thickness corresponding to each designated point as display 73 on the display.

The surgeon checks the map 70, the sectional image 71, the post-operative refractive power and the other data displayed on the display 43 to make sure that there is no problem. Having confirmed that there is no problem, the surgeon goes on to corneal surgery to ablate the cornea with an excimer laser beam. The surgeon operates the foot switch 7 to transmit laser irradiating signals to the control unit 40. Based on the obtained ablation data, the control unit 40 controls the irradiating optical system 25 (the driving circuits 47, 48 and 49) to perform ablation of the cornea in the way described later. In the case that the apparatus is not provided with the auto tracking mechanism, the alignment of the apparatus with the patient's eye needs to be performed again before irradiating the laser.

The control unit 40 drives the laser head 26 via the driving circuit 49 to emit the excimer laser beam. The emitted excimer laser beam is reflected and deflected by the mirror 27 and the dichroic mirror 17 and then converged by the lens 18. Thereafter, the control unit 40 drives the scanning mirrors 19 and 20 via the driving circuits 47 and 48 respectively so as to aim the excimer laser beam at any intended spot. Having reached the cornea E positioned at the focal point of the lens 18, the excimer laser beam is made scan by the scanning mirrors 19 and 20 in the two-dimensional directions within the determined irradiation (ablation) range. The scan with the excimer laser beam in the two-dimensional directions may be done in linearly directions similarly to the scanning with the infrared laser beam for the corneal shape measurement, or in concentrically directions (direction as if to draw concentric circles or a spiral).

Since the excimer laser is a pulsed laser, the depth that the laser is able to ablate is controlled by the number of the pulses (by the irradiation time). For this reason, the control unit 40 drives the laser head 26 via the driving circuit 49 to irradiate the excimer laser for the duration of the number of pulses (irradiation time) corresponding to the necessary ablation amount. The excimer laser being controlled in the aforementioned way is irradiated at each scanning spot within the irradiation (ablation) range so as to ablate the corneal tissue needs to be removed for the refractive error correction. AS the result, the patient's eye will have the intended refractive power.

Here, since the information about the corneal thickness is obtained, advantage of the information may be taken to perform surgery more appropriately. For example, comparison may be made between the determined amount of the cornea to be ablated and the thickness of the cornea to figure out the predicted thickness of the post-operative cornea (the thickness of the residual cornea after the ablation). If it is figured that the post-operative cornea is to be thinner than a predetermined standard, the irradiation of the laser is cancelled. Instead, the display unit 43 displays a warning or a not illustrated sound generator produce beep tones for warning. In addition, the laser head 26 and other components are controlled so as to irradiate the laser beam only when the thickness of the post-operative cornea is equal to, or thicker than the predetermined standard. This allows to eliminate the possibility of ablation when it should not be done. Further, the processing unit 42 may be made to adjust the ablation data (the irradiation range of the excimer laser and the like) so that the post-operative cornea is ensured to be thicker than the predetermined standard. The standard for the thickness of the post-operative cornea is determined with the use of the input unit 41.

Further, in the case of removing an affected part of the cornea such as opacity or the like, the irradiation conditions such as the irradiation range and the ablation depth are inputted by operating the input unit 41. In this case, also, the comparison is made between the determined amount of the cornea to be ablated and the thickness of the cornea. The irradiation of the laser beam is controlled based on the result of the comparison. In addition, instead of inputting the ablation depth, the thickness of the post-operative cornea may be inputted after confirming the pre-operative corneal shape displayed on the display unit 43.

As described above, if the optical axis of the measurement optical system 10 and that of the irradiation optical system 25 are made coaxial, a solution is presented to the conventional problem that the positional relationship between the patient s eye and the corneal shape measurement (topography) apparatus differs from the positional relationship between the patient's eye and the corneal surgery apparatus. In addition, the difference in the state of the patient's eye due to the difference in the position of the patient. The optical axis of the measurement optical system 10 and that of the irradiating optical system 25 do not necessarily have to be coaxial as long as the two optical axes have the known predetermined positional relationship therebetween. Yet, it is easier to control irradiation spot and the like if the two optical axes coincide with each other. In this embodiment, as for the irradiation method, the laser beam having a small circular section is scanned by the galvanomirror. Alternatively, it is possible to use a laser beam having a rectangle irradiating section and scan the laser beam in one direction by a mirror, or instead its scanning direction may be rotated by an image rotator or the like.

In addition, a solution is provided also to another problem associated with a conventional apparatus which combines a placido ring projecting unit and a TV camera provided in a topography apparatus for photographing its corneal reflex and a laser irradiating optical system and an observation optical system provided in a corneal surgery apparatus. Making the two optical axes coaxial solves this problem of complication and enlargement of the apparatus.

Still further, since the corneal thickness is obtained through measuring the three-dimensional shapes of the anterior and the posterior cornea, determination may be made as to whether to proceed with the ablation or to warn the surgeon when the thickness of the post-operative cornea is expected to be thinner than that of the standard post-operative cornea. This eliminates the possibility of ablation when it should not be done.

Still further, the auto-alignment and the auto-tracking by the eyeball position detecting optical system in this embodiment may possibly be omitted. Also, the display of the corneal shape data may be modified to display more variety of data. Still further, in the corneal shape measurement optical system 10, the projecting optical system that projects the infrared laser beam being the measurement light onto the cornea E and the optical system that directs the reflected right from the cornea E to the photo-detector 23 are partially shared with each other. However, the two optical systems may be replaced with two totally separated optical systems. Yet, even in this case, the pinhole 13 and the pinhole 22 have to be arranged conjugate with each other relative to the cornea E.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A corneal surgery apparatus which ablates corneal tissue with a laser beam, the apparatus comprising:
   a patient positioning unit on which a patient is placed on his back so that his eye faces upward;
   an irradiation unit including a light directing optical system for directing the laser beam to an intended range of a cornea of the patient's upward-facing eye, wherein the laser beam has a wavelength in a far ultra-violet region and an intensity capable of causing ablation to the irradiated corneal tissue;
   a corneal shape measurement unit which measures a three-dimensional shape of the upward-facing cornea, the corneal shape measurement unit including:
      a measurement light projecting optical system, including a first pinhole plate, for projecting a measurement light onto the upward-facing cornea, wherein a convergent point of the measurement light is shifted from an anterior surface of the cornea to a posterior surface of the cornea by moving a focusing lens along a central optical axis of the measurement light projecting optical system;
      wherein the central optical axis of the measurement light projecting optical system is made to be coaxial with a central optical axis of the light directing optical system midway on an optical path;
      a measurement light receiving optical system, including a second pinhole plate placed at a position conjugate with the first pinhole plate with respect to the cornea and a photo-detector for receiving reflected measurement light from the upward-facing cornea having passed through the second pinhole plate;
      wherein a central optical axis of the measurement light receiving optical system is divided from the central optical axis of the light directing optical system midway on an optical path;

a scanning unit which scans a projection spot of the measurement light on the upward-facing cornea in XY directions;

an arithmetic unit which performs arithmetic to obtain three-dimensional shapes of the anterior and posterior surfaces of the upward-facing cornea based on a position of the projection spot in the XY directions, a result detected by the photo-detector and a position to which the focusing lens is moved, and to obtain a thickness of the upward-facing cornea based on the obtained three-dimensional shapes of the anterior and posterior surfaces of the cornea; and a monitor unit which monitors a relationship between corneal ablation data and data about the thickness of the upward-facing cornea obtained by the corneal shape measurement unit.

2. The corneal surgery apparatus according to claim 1, further comprising:

input means for inputting at least one of a corrected refractive power to be acquired and post-operative corneal shape information; and arithmetic means for performing arithmetic to obtain the corneal ablation data from the inputted data and the three-dimensional shape of the anterior surface of the upward-facing cornea obtained by the corneal shape measurement unit;

wherein the monitor unit includes judgment means for judging whether or not a thickness of the post-operative cornea meets a predetermined standard based on the relationship between the ablation data and the data about the thickness of the upward-facing cornea; and informing means for informing a judgment result made by the judgment means.

3. The corneal surgery apparatus according to claim 1, further comprising:

input means for inputting at least one of a corrected refractive power to be acquired and post-operative corneal shape information; and arithmetic means for performing arithmetic to obtain corneal ablation data from the inputted data, the three-dimensional shape of the anterior surface of the upward-facing cornea and the data about the thickness of the upward-facing cornea.

4. The corneal surgery apparatus according to claim 1, further comprising:

input means for inputting at least one of a corrected refractive power to be acquired and post-operative corneal shape information; and arithmetic means for performing arithmetic to obtain the corneal ablation data from the inputted data and the three-dimensional shape of the anterior surface of the upward-facing cornea obtained by the corneal shape measurement unit;

wherein the monitor unit includes judgment means for judging whether or not a thickness of the post-operative cornea meets a predetermined standard based on the relationship between the ablation data and the data about the thickness of the upward-facing cornea; and irradiation control means for controlling operations of the irradiation unit in accordance with a judgment result made by the judgment means.

5. The corneal surgery apparatus according to claim 1, further comprising:

input means for inputting at least one of a corrected refractive power to be acquired and post-operative corneal shape information;

arithmetic means for performing arithmetic to obtain the corneal ablation data from the inputted data and the three-dimensional shape of the anterior surface of the upward-facing cornea obtained by the corneal shape measurement unit; and display means for graphically displaying the three-dimensional shape of the anterior surface of the upward-facing cornea obtained by the corneal shape measurement unit and the ablation data obtained by the arithmetic means in superposed relation with each other.

6. The corneal surgery apparatus according to claim 1, further comprising a display unit which graphically displays at least one of the three-dimensional shapes of the anterior and posterior surfaces of the upward-facing cornea obtained by the corneal shape measurement unit.

7. The corneal surgery apparatus according to claim 1, wherein the light directing optical system forms a small spot with the laser beam at an irradiation position on the cornea and shifts the spot of the laser beam in the XY directions.

8. The corneal surgery apparatus according to claim 7, wherein the light directing optical system comprises a focusing optical lens by which the small spot is formed with the laser beam on the cornea and the spot of the laser beam is shifted in the XY directions, and the focusing optical lens is moved along the central optical axis of the light directing optical system in accordance with a position of the cornea in a Z direction.

9. The corneal surgery apparatus according to claim 1, wherein the light directing optical system comprises a scanning optical unit which forms a small spot with the laser beam at an irradiation position on the cornea and shifts the spot of the laser beam in the XY directions.

10. The corneal surgery apparatus according to claim 9, wherein the scanning unit is disposed on the coaxial central optical axes of the light directing optical system and the measurement light receiving optical system, and the scanning optical unit is shared with the scanning unit.

11. A corneal surgery apparatus which ablates corneal tissue with a laser beam, the apparatus comprising:

a patient positioning unit on which a patient is placed on his back so that his eye faces upward;

an irradiation unit including a light directing optical system for directing the laser beam to an intended range of a cornea of the patient's upward-facing eye, wherein the laser beam has a wavelength in a far ultra-violet region and an intensity capable of causing ablation to the irradiated corneal tissue;

a corneal shape measurement unit which measures a three-dimensional shape of the upward-facing cornea, the corneal shape measurement unit including:

a measurement light projecting optical system, including a first pinhole plate, for projecting a measurement light onto the upward-facing cornea, wherein a convergent point of the projected measurement light is shifted from an anterior surface of the cornea to a posterior surface of the cornea by moving a focusing lens along a central optical axis of the measurement light projecting optical system;

wherein the central optical axis of the measurement light projecting optical system is made to be coaxial with a central optical axis of the light directing optical system midway on an optical path;

a measurement light receiving optical system, including a second pinhole plate placed at a position conjugate with the first pinhole plate with respect to the cornea and a photo-detector for receiving reflected measurement light from the upward-facing cornea having passed through the second pinhole plate;

wherein a central optical axis of the measurement light receiving optical system is divided from the central optical axis of the light directing optical system midway on an optical path;

a scanning unit which scans a projection spot of the measurement light on the upward-facing cornea in XY directions; and an arithmetic unit which performs arithmetic to obtain the three-dimensional shapes of the anterior and posterior surfaces of the upward-facing cornea based on a position of the projection spot in the XY directions, a result detected by the photo-detector and a position to which the focusing lens is moved, and to obtain a thickness of the upward-facing cornea based on the obtained three-dimensional shapes of the anterior and posterior surfaces of the cornea; and arithmetic means for performing arithmetic to obtain an ablation amount at each position of the cornea based on the three-dimensional shape of the anterior surface of the upward-facing cornea and the thickness of the upward-facing cornea obtained by the corneal shape measurement unit.

* * * * *